(12) United States Patent
Maldonado

(10) Patent No.: US 7,605,291 B2
(45) Date of Patent: Oct. 20, 2009

(54) METHOD FOR THE PREPARATION OF VOLATILE ANESTHETICS

(76) Inventor: Adalberto Maldonado, 95 Calle Rafael coca Navas, Urb. Quintas las Muesas, Cayey, PR (US) 00736

(*) Notice: Subject to any disclaimer, the term of this patent is extended or adjusted under 35 U.S.C. 154(b) by 28 days.

(21) Appl. No.: 11/740,576

(22) Filed: Apr. 26, 2007

(65) Prior Publication Data

US 2007/0255077 A1    Nov. 1, 2007

Related U.S. Application Data

(60) Provisional application No. 60/795,480, filed on Apr. 27, 2006.

(51) Int. Cl.
*C07C 45/83* (2006.01)
*G06F 19/00* (2006.01)

(52) U.S. Cl. .......................... 568/411; 702/22

(58) Field of Classification Search ................ 568/411
See application file for complete search history.

(56) References Cited

U.S. PATENT DOCUMENTS

| | | | |
|---|---|---|---|
| 2,855,344 A * | 10/1958 | Andre | .......................... 203/17 |
| 3,668,256 A * | 6/1972 | Brundege | .................... 568/411 |
| 3,720,587 A | 3/1973 | Croix | |
| 3,726,268 A | 4/1973 | Stansell | |
| 3,846,332 A | 11/1974 | Croix | |
| 3,897,502 A | 7/1975 | Russell et al. | |
| 4,626,600 A * | 12/1986 | Fulmer et al. | ................ 568/411 |
| 4,762,856 A | 8/1988 | Terrell | |
| 4,855,511 A | 8/1989 | Halpern et al. | |
| 4,874,901 A | 10/1989 | Halpern et al. | |
| 4,972,040 A | 11/1990 | Robin et al. | |
| 5,015,781 A | 5/1991 | Robin et al. | |
| 5,026,924 A | 6/1991 | Cicco | |
| 5,205,914 A | 4/1993 | Rozov et al. | |
| 5,283,372 A | 2/1994 | Rozov et al. | |
| 6,054,626 A | 4/2000 | Chambers et al. | |
| 6,303,826 B1 * | 10/2001 | Bhinde et al. | ................ 568/411 |

OTHER PUBLICATIONS

"Emerson Releases New DeltaV PredictPro Model Predictive Control Software Application," Emerson Process Management Press Release (Aug. 6, 2003).
"Using Model Predictive Control-Based PAT to Optimize Distillation," *Pharmaceutical Manufacturing*, p. 46 (Jan. 2006).
Dierking (ed.), "Dow Chemical and Baxter Healthcare Win CP's Inaugural Plant Innovation Award," *Chemical Processing*, pp. 19-22 (May 2005).

* cited by examiner

*Primary Examiner*—Sikarl A Witherspoon
(74) *Attorney, Agent, or Firm*—Marshall, Gerstein & Borun LLP

(57) ABSTRACT

The present invention is concerned with the automated control of the synthesis and purification of components useful in the synthesis and purification of volatile anesthetics. The invention is particularly useful in its application to the purification of acetone used in the purification of isoflurane.

3 Claims, 3 Drawing Sheets

The MPC control block monitors four inputs and manipulates two outputs on the acetone column. Nearly 600 consecutive batches have been within specification since MPC was implemented.

METHOD FOR THE PREPARATION OF VOLATILE ANESTHETICS

CROSS-REFERENCE TO RELATED APPLICATIONS

This application claims the benefit of U.S. Provisional Patent Application Ser. No. 60/795,480, filed Apr. 27, 2006.

BACKGROUND OF THE INVENTION

1. Technical Field

The present invention is concerned with process control synthesis of volatile anesthetics. Volatile anesthetics generally include desflurane, sevoflurane, isoflurane, enflurane and nitrous oxide. Synthesis of the widely used anesthetics desflurane, sevoflurane and isoflurane involve the chlorination and fluorination of precursor molecules to eventually yield the final products.

2. Background Art

Commercially available volatile fluorinated anesthetics include desflurane ($CF_3CHFOCHF_2$), enflurane ($CHClFCF_2OCHF_2$), halothane ($CF_3CHBrCl$), isoflurane ($CF_3CHClOCHF_2$) and sevoflurane (($CF_3$)$_2CHOCH_2F$). The physical properties of volatile fluorinated anesthetics are important to the anesthesiologist. These physical properties include boiling point, specific gravity, vapor density, vapor pressure, oil/gas partition coefficient and blood/gas partition coefficient (percent of the anesthetic found in a known quantity of blood versus the percent found in a known volume of atmosphere above the blood sample).

Although each of the molecules depicted above has its own unique characteristics that provide a set of parameters needed to commercially develop it as an anesthetic, the chemical properties and chemical purity of the fluorinated volatile anesthetic are particularly important.

The chemical purity of the fluorine substituted volatile anesthetic is of utmost importance, requiring clean methods of production and extensive manufacturing controls. Additionally, the synthesis of these anesthetics requires consideration of many factors not normally encountered in the medicinal chemistry arena, i.e., the need to produce millions of pounds of pharmaceuticals with the highest standards of purity. Accordingly, it is highly desirable to find synthetic routes that give high purity fluorine substituted volatile anesthetics.

Desflurane, 2-(difluoromethoxy)-1,1,1,2-tetrafluoroethane, is an inhalation anesthetic possessing very advantageous properties. Desflurane is of significant commercial value, in particular, as a result of being an effective anesthetic which demonstrates rapid induction and an unexpectedly rapid recovery from anesthesia. The latter property makes it especially attractive for surgical procedures done on an outpatient basis. The use of desflurane as an inhalation anesthetic is claimed in Terrell, U.S. Pat. No. 4,762,856, issued Aug. 9, 1988. Desflurane was originally disclosed in Example XXI of Russell et al U.S. Pat. No. 3,897,502, issued Jul. 29, 1975, which is directed to a method of fluorinating ethers to make compounds generally useful as solvents, degreasing agents and the like.

More recently, a number of processes for preparing desflurane have been patented. Halpern et al, U.S. Pat. No. 4,855,511 discloses preparing desflurane by the reaction of a compound having the formula $CHCl_2OCHClCOCl$ with sulfur tetrafluoride at elevated temperatures. Halpern et al, U.S. Pat. No. 4,874,901 discloses a method of fluorinating a chlorine on the carbon adjacent the ether oxygen in chloro-fluoro ethers by reaction with sodium or potassium fluoride at elevated temperature and pressure in the absence of solvent. By this method, isoflurane is converted to desflurane.

In Robin et al, U.S. Pat. No. 4,972,040, fluoral methyl hemiacetal, $CF_3CH(OH)OCH_3$, is reacted with p-toluene sulfonyl chloride to form the corresponding tosylate compound. The tosylate group is then removed by reaction with a fluorinating agent to form $CF_3CHFOCH_3$. This compound is converted to desflurane by chlorinating the methyl group, preferably with chlorine gas, followed by reaction with a fluorinating agent.

Robin et al. U.S. Pat. No. 5,015,781, disclosed a process for forming desflurane by the direct fluorination of isoflurane by bromine trifluoride. Cicco, U.S. Pat. No. 5,026,924, discloses a low temperature preparation of desflurane comprising reacting isoflurane with hydrogen fluoride in the presence of a catalyst comprising antimony pentachloride, alone or in combination with antimony trichloride.

Rozov et al., U.S. Pat. No. 5,283,372 discloses the preparation of desflurane by reacting an optically pure isoflurane with bromide trifluroide to yield a corresponding optically pure desflurane. Chambers et al., U.S. Pat. No. 6,054,626, discloses the preparation of desflurane by reacting $CF_3CH_2OCHF_2$ with Cobalt trifluoride. Rozov et al., U.S. Pat. No. 5,205,914, discloses the preparation of desflurane by using the starting material hexafluoropropene.

Isoflurane synthesis and purification methods are disclosed in U.S. Pat. No. 3,720,587; 3,726,268; and 3,846,332.

During 2003, 615 batches of acetone from an isoflurane purification process were processed by Baxter Healthcare Corporation (Guayama, Puerto Rico), 18 of which failed the water specification, leading to significant delays pending the investigation and documentation of each failed batch. There is, therefore, a need for an improved processes for the synthesis and purification of volatile anesthetics.

SUMMARY OF THE INVENTION

The present invention provides a method for controlling the synthesis and purification of volatile anesthetics. In an embodiment, the present invention controls the distillation of volatile agents useful in the synthesis and purification of volatile anesthetics.

In an embodiment, the present invention provides a method of using a control module to automate and, therefore, improve the efficiency of a distillation process of volatile agents useful in the preparation of isoflurane.

In an embodiment, the present invention provides a method for controlling the separation of acetone and water wherein the flow of the acetone/water mixture to a distillation apparatus is controlled and steam heat for affecting the distillation of the mixture is controlled by a computer.

The present invention provides greater purity acetone collection from a automated still. Preferably, the water content in the collected acetone is 3 percent by weight or less.

DETAILED DESCRIPTION OF THE INVENTION

The present invention is susceptible of embodiments in many different forms. Preferred embodiments of the invention are disclosed with the understanding that the present disclosure is to be considered as exemplifications of the principles of the invention and are not intended to limit the broad aspects of the invention to the embodiments illustrated.

Figure 1:
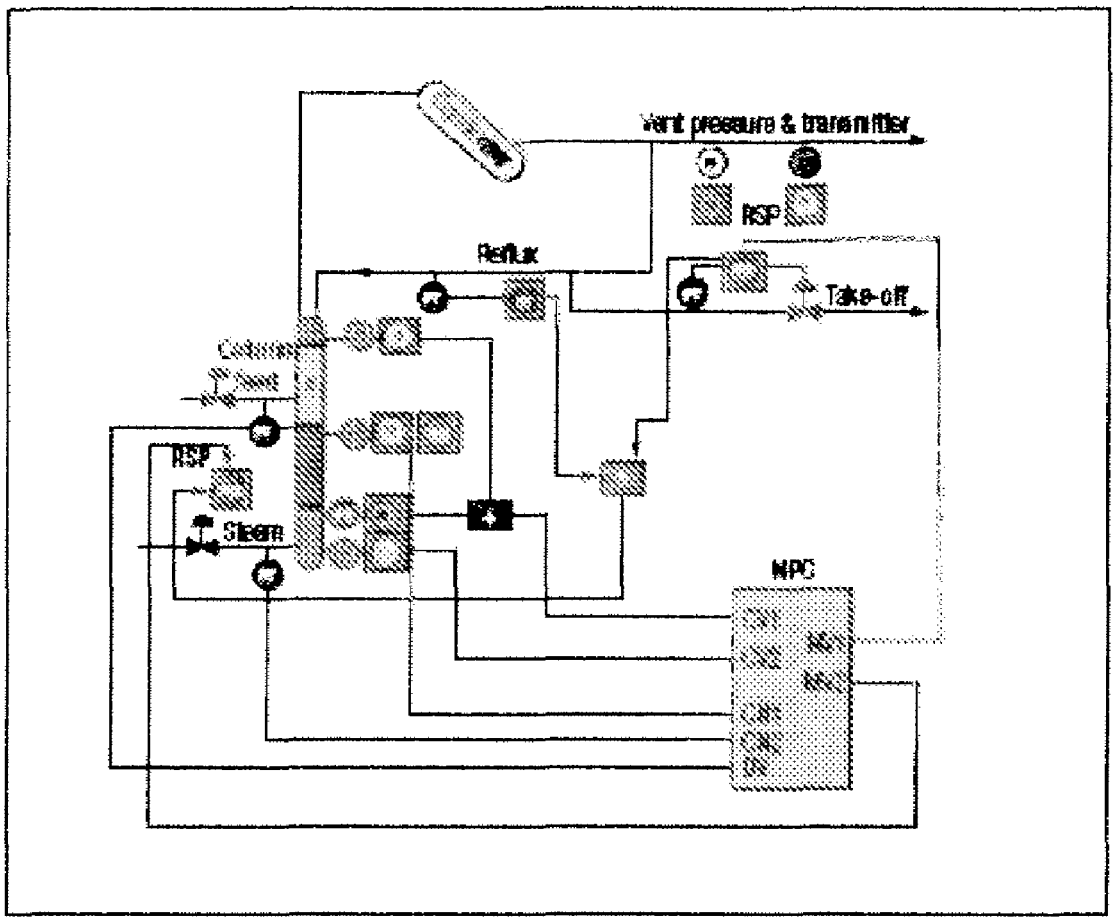
FIG. 1 is a block diagram of the acetone recovery system run by a controller employing a controller (MPC).

As illustrated in FIG. 1, the present invention is directed to a method for the automated control of a distillation still useful in the recovery of volatile agents used in the synthesis and purification of volatile anesthetics. The present invention employs a controller, typically operated by a microprocessor-based system, e.g., a computer, useful in the automated control of the synthesis and purification of various components used in the synthesis and purification of volatile anesthetics.

The controller has inputs and outputs. The inputs are signals received from various sensing devices useful in monitoring the progress of various subsystems in the overall synthesis and purification of a pharmaceutical agent. Such inputs generally will be electrical signals received from sensing devices including, but not limited to, transducers, temperature probes, flow meters, weight scales and other sensing devices used in chemical processing.

The outputs of the controller are generally electrical signals directing various receiving devices to open, close or partially open or close a valve, and increase or decrease the temperature of a heating or cooling system. Examples of receiving devices include, but are not limited to, automated valves.

The controller is programmed by an operator to control the still in such a way as to yield the highest desired product concentrations of separated components. Thus, the controller will be programmed with an algorithm useful in achieving the desired result. In operation, the controller continually receives input data, stores that data in a data memory and operates the algorithm. The algorithm continually calculates output values based on the continuous flow of data input. Therefore, according to the inputs and the algorithm, the controller will send outputs to the various receiving devices in order to adjust the processing conditions of the still in order to yield the desired separation results. An example of controller is the DeltaV controller from Emerson Process Management (Austin, Tex.). An example of software useful in the present invention is the Model Predictive Control (MPC) software also available from Emerson. The MPC can be programmed with data from a statistical process control (SPC) of empirical data, an application of statistical methods to identify and control the special cause of variation in a process.

Figure 2:
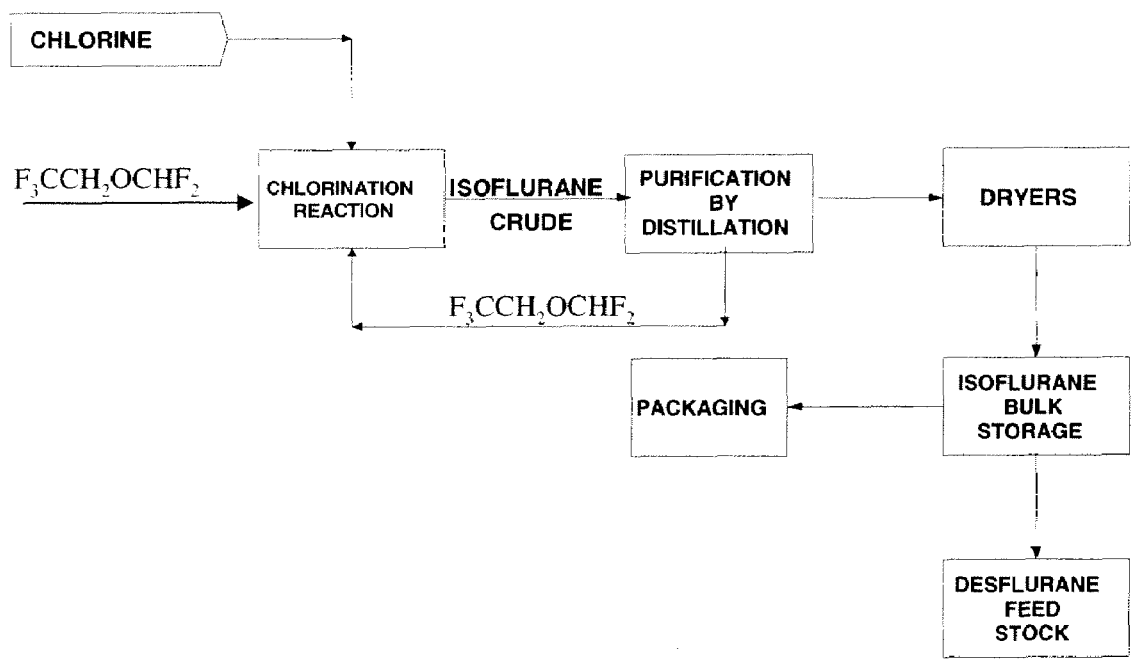
FIG. 2 is a block diagram of the synthesis of isoflurane from the reaction of 2,2,2,-trifluoroethyl difluoromethyl ether and chlorine.

The present invention can be applied to any number of such separations as part of a pharmaceutical synthesis. One synthesis and purification system useful for application of the present invention is illustrated in FIG. 2. As shown in FIG. 2, isoflurane is synthesized from the reaction of 2,2,2,-trifluoroethyl difluoromethyl ether and chlorine. The purified isoflurane can then be packaged and sold as a volatile anesthetic or can be used as a reagent in the synthesis of desflurane. As part of the isoflurane synthesis, isoflurane is purified by azeotropic distillation with acetone. Spent acetone contains water and therefore needs to be purified and recycled in the continuous isoflurane purification process. The use of a distillation still, as illustrated in FIG. 3, is employed in such acetone purification.

Figure 3:
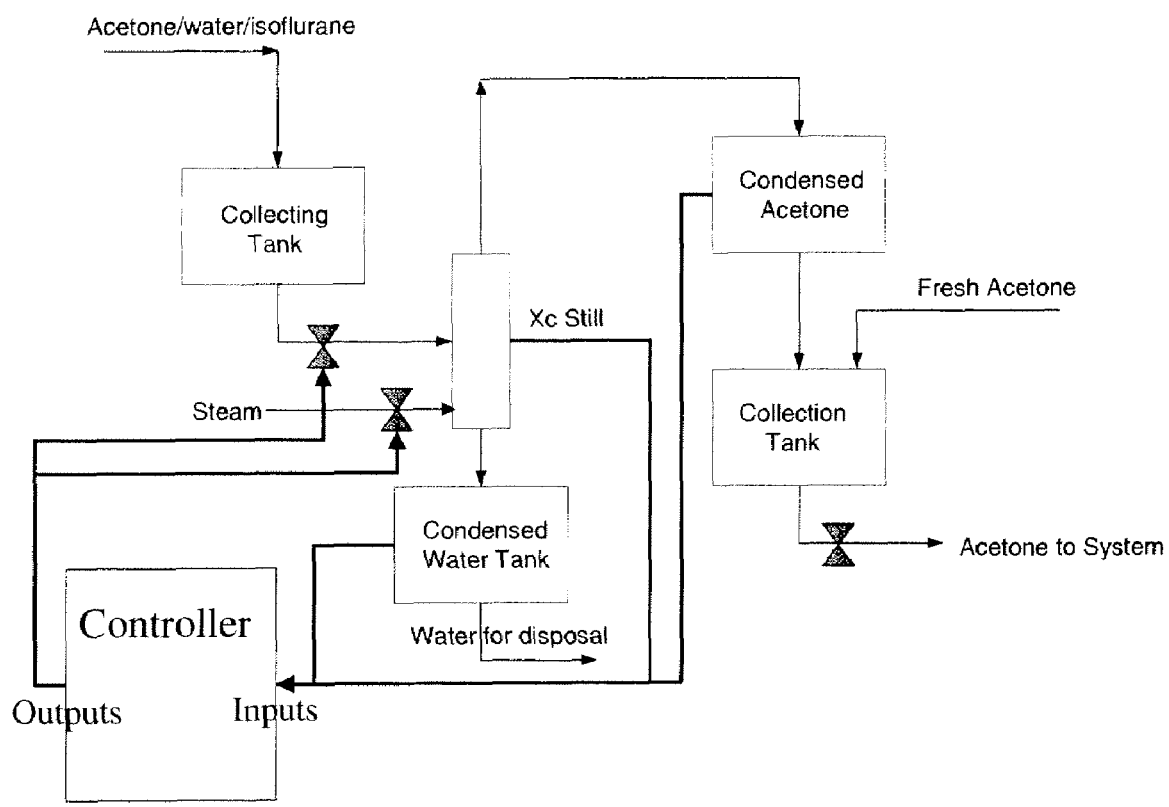
FIG. 3 is a block diagram of the use of a controller in the distillation recovery of acetone from a crude of water and acetone.

As shown in FIG. 3, acetone and water are collected in a collecting tank. A fluid line from the collecting tank to the Xc still is interrupted by an automated valve. The automated valve is actuated by the controller and the rate and volume of the acetone/water mixture is controlled as it enters the still. The Xc still is comprised of a column containing enclosed fluid lines of steam for heating. The steam lines entering the column of the still are also interrupted by an automatic valve, controlled by the controller. The controller, therefore, controls the volume and rate of steam entering the steam line of the still and thereby controls the temperature of the column.

The Xc still has two outputs, one entering a condenser for the condensation of vapor acetone and the other for collecting water separated by the still. The condensed acetone drains into a collection tank for introduction back into the isoflurane purification process and the water drains into a collection tank for disposal.

The present invention improves the acetone purity, based on water content, of the acetone collected from the still. Preferably, the acetone collected will have a water content of 5% or less by weight and more preferably, 3% or less by weight.

EXAMPLE 1

Engineers at Baxter improved the operation of an acetone recovery column (the Xc still) through use of MPC. The throughput and quality of acetone increased and failed batches were eliminated, thereby making it unnecessary for Baxter engineers to spend time documenting and investigating off-spec material.

The Xc still recovers acetone from the effluent of an upstream column for reuse (see FIG. 1). The recovered acetone must meet a specification of less than 3 wt-% water.

The team used SPC to analyze data from 140 batches, which showed that the acetone had an average water content of 2.3 wt-%, a Cp (Process Capability index: in Six Sigma statistical analysis—the ratio between the permissible spread and the actual spread of a process.) of 1.24 and Cpk (Process Capability index: in Six Sigma statistical analysis—taking account of off-centredness, effectively the Cp for a centered process producing a similar level of defects) of 0.54. A low Cp indicates a high degree of spread in the data (a Cp of 2 or greater corresponds to Six Sigma performance, an engineering process control system known to those skilled in the art), whereas the higher the Cpk, the closer the data are to the target. Hence, the data from these batches indicated a lack of control and significant room for improvement.

The first step toward improving column operation was to reconfigure the control scheme and improve the tuning so it could run in automatic mode. Despite the fact that six batches exceeded the 3 wt-% water specification, data from 125 batches showed a 35% reduction in average water content to 1.5 wt-%. Although the average water content went down (Cpk=0.86), the spread in the data increased (Cp=0.88).

Other columns onsite were controlled using MPC, so the team decided to implement it on the Xc still. MPC is an add-on module available from Emerson for the DeltaV distributed control system (DCS). The module enables concurrent control of multiple process constraints, rather than managing them as individual loops or variables. One block can monitor up to four different variables and anticipate the expected behavior, thereby applying several corrective outputs as necessary to maintain the optimal column performance. The control is employed to monitor four inputs and two outputs on the acetone column.

Once MPC was employed, the average water content of 31 consecutive batches was reduced to 1.2 wt-%—none of them failed—and SPC showed a Cp of 8.98 and Cpk of 7.39. There have been no failures since MPC was implemented, over 600 consecutive batches have been within specification.

What is claimed is:

1. A method for controlling the separation of acetone from water comprising:
   a. adding a mixture of acetone and water to a heating column;
   b. heating the column with an enclosed steam line to create acetone vapor and liquid water;
   c. condensing the acetone vapor into purified liquid acetone with a condenser;
   d. collecting the liquid acetone in a first tank and collecting the liquid water in a second tank;
   e. measuring temperature, pressure and flow of the mixture of acetone and water of step a and the steam of step b;
   f. receiving the temperature, pressure and flow measurements by a computer;
   g. inputting the temperature, pressure and flow measurements into a statistical process control software running on the computer; and
   h. controlling the addition of the mixture of acetone and water in step a and the addition of steam in step b by the computer.

2. The method of claim 1, wherein the acetone collected has a water content of less than 5 percent by weight.

3. The method of claim 1, wherein the acetone collected has a water content of less than 3 percent by weight.

* * * * *